(12) United States Patent
Korpela

(10) Patent No.: US 9,463,457 B2
(45) Date of Patent: Oct. 11, 2016

(54) MECHANICAL WASHING AND MEASURING DEVICE FOR PERFORMING ANALYSES

(71) Applicant: Timo Kalevi Korpela, Turku (FI)

(72) Inventor: Timo Kalevi Korpela, Turku (FI)

(73) Assignee: Conventa Ltd., Turku (FI)

( * ) Notice: Subject to any disclaimer, the term of this patent is extended or adjusted under 35 U.S.C. 154(b) by 64 days.

(21) Appl. No.: 14/376,445

(22) PCT Filed: Feb. 1, 2013

(86) PCT No.: PCT/FI2013/000006
§ 371 (c)(1),
(2) Date: Aug. 4, 2014

(87) PCT Pub. No.: WO2013/113983
PCT Pub. Date: Aug. 8, 2013

(65) Prior Publication Data
US 2015/0017641 A1    Jan. 15, 2015

(30) Foreign Application Priority Data
Feb. 3, 2012 (FI) ................................. 20120036

(51) Int. Cl.
*B01L 3/00* (2006.01)
*G01N 33/543* (2006.01)
*G01N 21/03* (2006.01)

(52) U.S. Cl.
CPC .............. *B01L 3/502* (2013.01); *B01L 3/5023* (2013.01); *G01N 33/54366* (2013.01); *B01L 3/5082* (2013.01); *B01L 2300/044* (2013.01); *B01L 2300/0636* (2013.01); *B01L 2300/087* (2013.01); *B01L 2300/0867* (2013.01); *B01L 2400/0478* (2013.01); *G01N 2021/0325* (2013.01)

(58) Field of Classification Search
CPC B01L 3/502; B01L 3/5023; G01N 33/54366
See application file for complete search history.

(56) References Cited

U.S. PATENT DOCUMENTS

| 5,744,096 A | 4/1998 | Jones et al. |
| 2003/0180815 A1 | 9/2003 | Rawson et al. |
| 2005/0186111 A1 | 8/2005 | Wang et al. |
| 2011/0290669 A1 | 12/2011 | Davis et al. |
| 2012/0192628 A1* | 8/2012 | Liu ........................ B01L 3/502 73/64.56 |

FOREIGN PATENT DOCUMENTS

| EP | 0378353 | 7/1990 |
| WO | 9706428 | 2/1997 |
| WO | 2011003281 | 1/2011 |

OTHER PUBLICATIONS

International Search Report of PCT/FI2013/000006 dated on May 20, 2013.

* cited by examiner

*Primary Examiner* — Jill Warden
*Assistant Examiner* — Julie Tavares
(74) *Attorney, Agent, or Firm* — Berggren, Inc.

(57) ABSTRACT

The invention describes simple and reliable cartridge constructions for carrying out analytical procedures in a closed system, especially for carrying out bioaffinity analyses. The cartridge exploits a measuring component, or a test strip (1 in FIG. 1) and its cover (2 in FIG. 1) as well as the motion between these two components to achieve liquid flow and events which are necessary for the analysis.

20 Claims, 3 Drawing Sheets

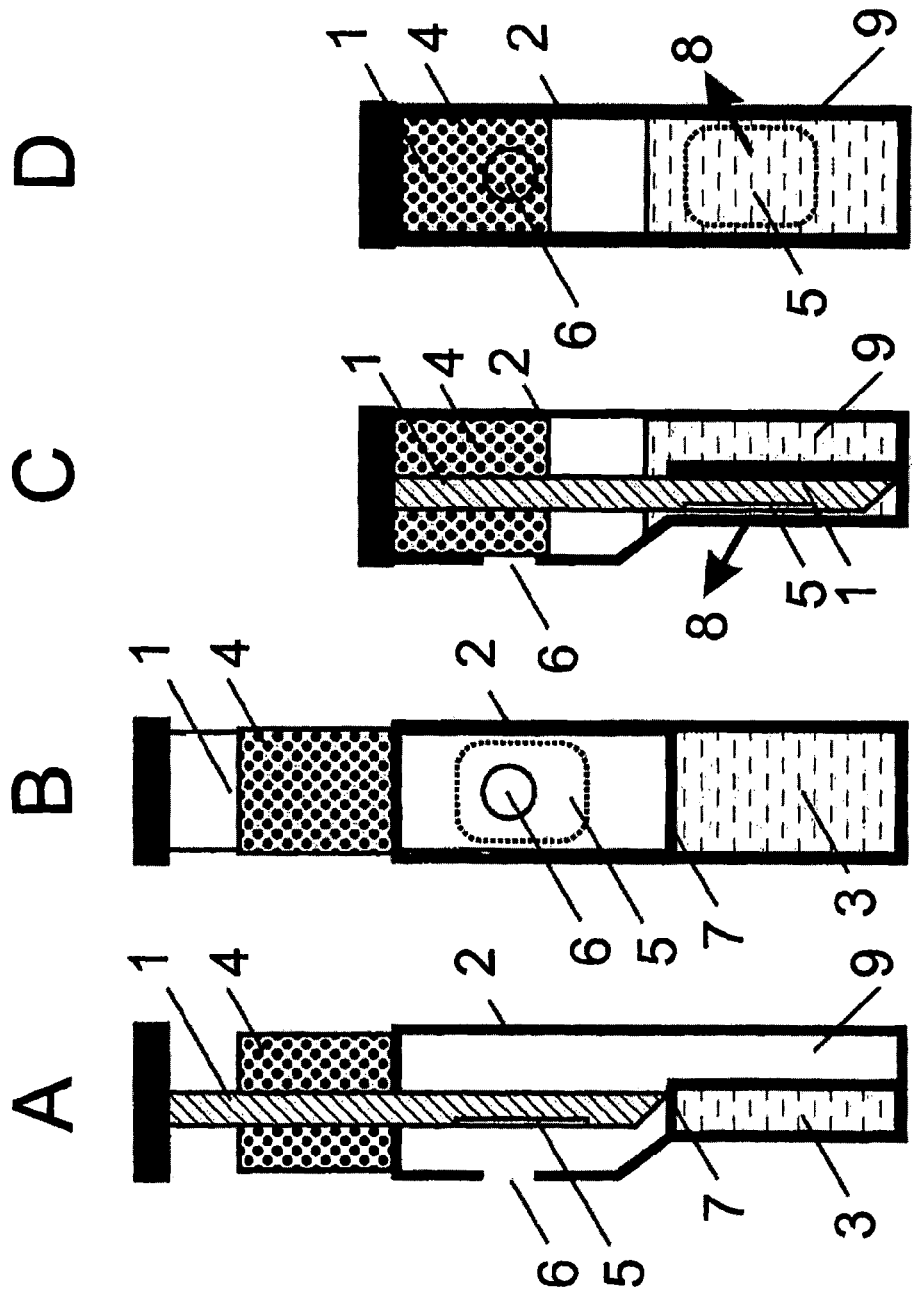
Figure 1 (A-D)

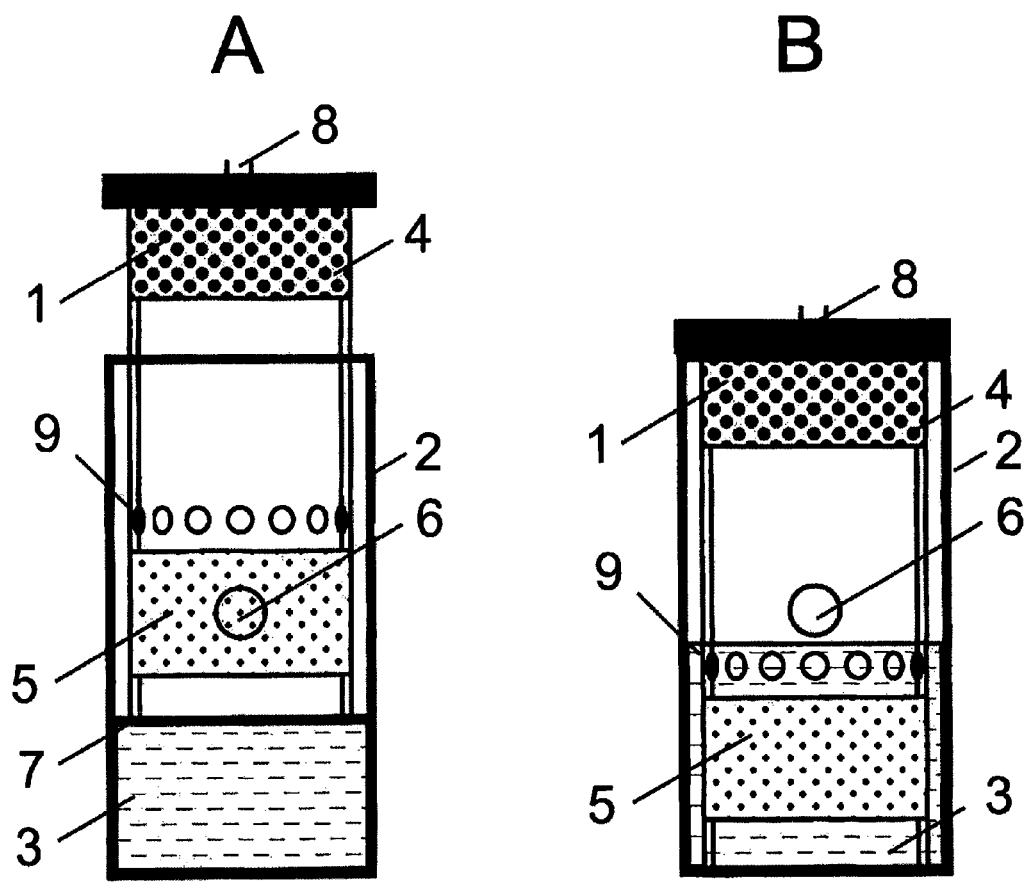
Figure 2 (A and B)

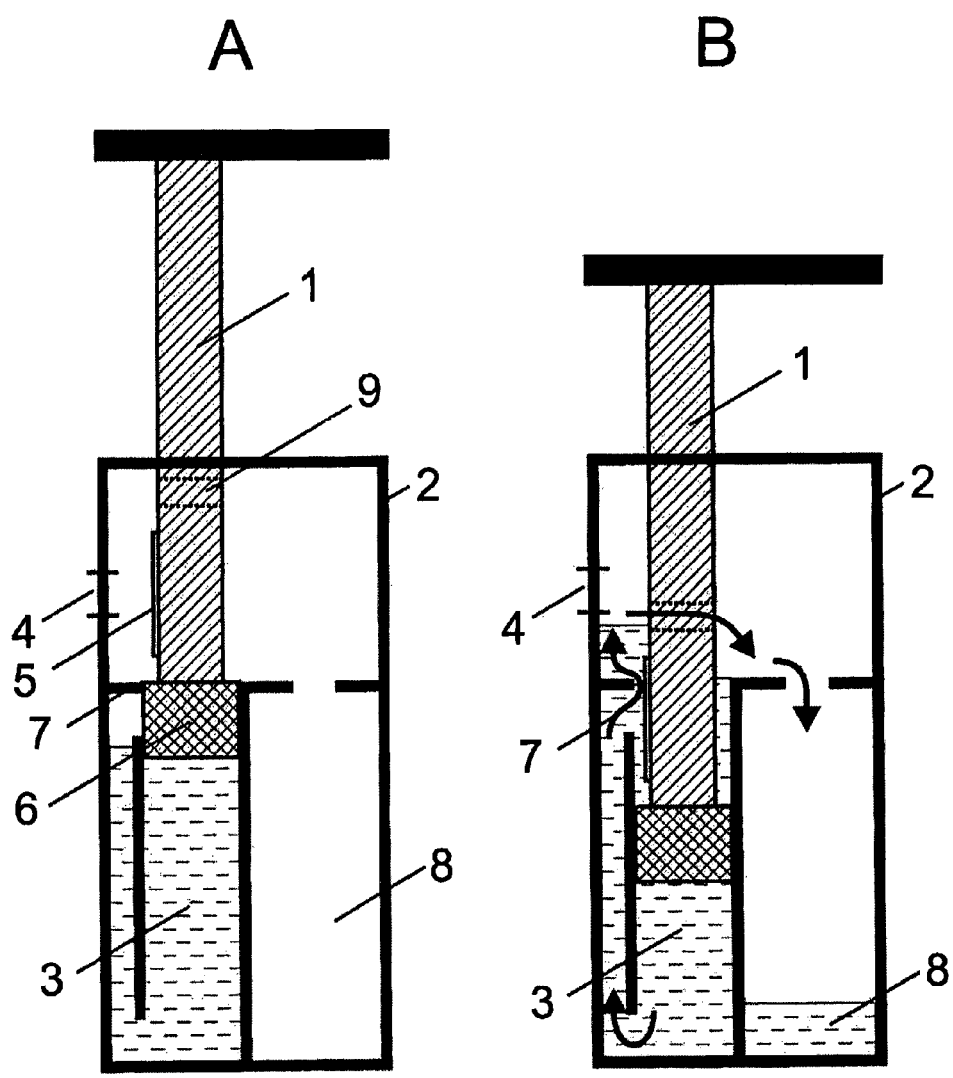
Figure 3 (A and B)

MECHANICAL WASHING AND MEASURING DEVICE FOR PERFORMING ANALYSES

PRIORITY

This application is a national entry of PCT/FI2013/000006 filed on Feb. 1, 2013 which claims priority of FI20120036 filed on Feb. 3, 2012 both of which are fully incorporated herein by reference.

FIELD OF INVENTION

The invention is focused to deal with a mechanical device, which performs analyses in a chamber which enables washing and measuring steps to be done so that liquid is not added or removed from the chamber. The described invention can be exploited as a single-use analytical device especially in hospital laboratories and doctors' offices.

BACKGROUND OF THE INVENTION

When diagnosing human and animal diseases, as well as, performing various other analytical tasks in laboratories, each individual analysis is often attempted to be done in a separate closed measuring cell (chamber, cassette, or cartridge are also used as the synonyms). This will reduce the contamination risk between different samples (e.g. DNA analyses) and increase the safety of the personnel (microbiological samples, poisons).

Measuring cell is defined as a relatively small device to which the sample to be analyzed will be introduced. After the sample, various processes are made which effect movements of reacting components and liquids by employing pumps from outside or inside of the cell, or capillary, centrifugal, electrical, or magnetic forces are exploited. After these procedures, the measurement itself can take place inside or from outside of the cell. The measuring cell should be small and the measuring procedure must be reproducible even the samples are from different sources and therefore having different properties. For example, different human individuals may have body fluids which differ in viscosity or capillary properties and this can harm or prevent getting reproducible results. The drawback of applying outside pumps (suction or pressure) lies in their complexity since the pump must be mechanically joined to the measuring cell. Contamination risks may also appear at this stage. The drawback of internal micro pumps is their high price and poor reliability. When using small channels in transferring liquids, viscosity and capillary forces always interfere even if the liquid movement is forced by pumps or centrifugal forces.

Several projects are globally underway targeting to analyses made in closed cassettes or cells including liquids and reagents stored inside the cell ("all-in-one" cassette). Such projects are usually based on applying microfluidistic technologies. The gathered experience, however, shows that microfluidistic devices are very difficult to produce industrially so that they equally from cell to cell and especially from batch to batch of then devices. Very small channels in the devices bring drawbacks which origin from qualitatively different laws of micro/nano world compared to the usual macro world. The phenomena are difficult to control because they are result from many parameters including surface tension, capillary forces, viscosity, osmotic pressure, electrolyte composition, temperature and/or material surface changes. The colligative properties of liquids always deviate from ideal solutions, especially in the case of complex biological samples.

The analytical tests which especially benefit from closed measuring cells are those dealing with substances which cause big risks for infection, for example, when dealing with blood samples from patients carrying potentially dangerous microbes or viruses. In such cases, no material must not escape from the measuring cell. Biological and chemical toxins belong to the same category. The methods based on nucleic acids recognition are extremely interference-sensitive and even micro or nano droplets can contaminate the laboratory and hence cause occasional false results for a long future time. To overcome the problems necessitate performing of a profound cleaning process in the laboratory. The diagnostic tests made at doctors' offices (so-called point-of-care, POC) do not necessarily belong to very dangerous ones, but thereby the use of measuring cells can make the performance of the analyses simple and uneducated technical assistants can do the test. The small size of the measuring cell used in POC need not to be advantageous because the cell must be convenient to be manipulated. According to the present invention, the small size of the measuring cell is not the special objective but to have a handy device which can be easily manipulated. Therefore, the drawbacks originating from micro and nano structures can be in a great extent avoided by the present invention.

The closest inventions to the present one could be illustrated by the following patent publications. US 2005186111A1 (2005, Wang Naishu et al) describes an interrupted immunological testing device. WO 2011003281 A1 (2011, Alere Switzerland GMBH) describes a construction of detection device having two vessels which can be mechanically inserted to each other. US 2003180815 A1 (2003, Rawson Keith et al.) describes a lateral flow test strip and a reagent storage blister. Constructions in U.S. Pat. No. 5,744,096 A (1998; Jones Rold et al.) and US 2011290669 A1 (2011, Davis Graham et al.) applied movable components to carry out immunoassays. The drawback in all these five related inventions is that they are technically very demanding to manufacture and therefore the advantages over the existing micro-fluidistic measuring cells remain marginal. In addition, the cited patent publications do not describe all the essential technical features of the present invention.

The before-described problems of washing, measurement, and contamination can be avoided, according to the present invention, by a closed single-use measuring cell, which does not contain microchannels and which is made enough large in size to be easily manipulated. The invention exploits a simple, easily fabricable mechanical pump for moving liquids. The pump itself serves as an active part of performing the analysis. The pump contains two parts, which can be described as a "cylinder" and a "piston". The pumping effect is achieved by pressing the piston into a liquid reservoir inside the cylinder part. This process includes events which are required to fulfill the analysis. The process leads to obtaining of analytically meaningful results. The typical features of the invention are further described in the patent claims.

BRIEF DESCRIPTION OF FIGURES

FIG. 1. FIG. A is the front-view of the measuring cell before analysis. FIG. B shows the side-view. FIG. C (front view) shows the cell before the measurement (i.e. at the end of the movements) and FIG. D is the same from side. The terms of "up" and "down" are used thereinafter only for clarity reasons assuming that the device stands as drawn in the Figs. The numbering is as follows: 1, the part of the measuring cell (test strip) which functions like a piston. It can be plunged into the vessel 2 (i.e. the container for 1, cartridge casing or "cylinder") down to liquid container, blister, or reservoir (3). Leakage of liquid from (2) is prevented with liquid-absorbing material (4) which moves together with the cover of (2) down inside of (2) when (1) is pressed down. The piston (1) contains active surface (5) necessary to the analytical procedures. The sample is inserted onto (5) through a hole or slot (6) of (2). The reservoir (3) can contain one or more of liquid compartments preferably separated with a film which can be broken when the piston (1) is pressed forward (usually down). The tip of the lower part of (1) is shaped in such a way that when the piston is pushed down, the protruding liquid is directed to wash the active surface (5). In the measurement position (C and D), the analytically active surface (5) locates in front of the sample window allowing light detection through the window. The side of the piston (1) moves in a respective groove in the cylinder (2) which guides smooth and accurate movement of (2; not shown in Figs). When the piston is at the down position (measurement position) and extension on the piston (just above the active surface, not drawn in the Figs for clarity) will lock the liquid reservoir. The Figures do not define the sizes and exact relations of the measures of the components. They can be altered according to the applications and methods of measurement. The drain holes above and/or sides of the active surface (5) are not also shown in FIG. 1 for clarity. In FIG. 1, C and D, the arrow 8 describes the light generated from the measuring step, for example, luminescence after excitation of luminophoric label molecules. In FIG. 1, A and D, part 9 illustrates the space where the washing liquid can be introduced (illustrated in FIG. 3 by arrows). Reservoir 9 may contain a liquid absorbing material. In Fig A, the used washing liquid can also locate in the space in the chamber above the active surface or the liquid can be absorbed into material (4), and thereby (2) can be realized more simply.

FIG. 2. Measuring cell made of two cylinders inserted one inside the other. The measuring cell functions as in FIG. 1. In FIG. 2 A, the cell is up and ready for sample application. FIG. 2 B illustrates the cell ready for the measurement. In the FIG. 2, the active surface (5) can be around the whole cylinder. The active surface is preferably in a niche of the piston and then the surface will not be prone to mechanical scratches from movements of the inserted tubes. The sample is applied through hole (6) to the active surface (5). The hole is covered with a stopper which is taken off when the sample is applied. This construction allows penetration of the sample by capillary forces over the space between the two cylinders. The distance between piston and cylinder is optimally 0.1-2.5 mm. Extra sample is leaking through holes (9) into the inner cylinder (serving as the waste storage). The inner cylinder is closed in down part but the upper part has a small hole for air (8) and a porous absorbing stopper which prevents liquid to spill off if the cell is turned upside down. In FIG. 2 the liquid reservoir (3) is tightened between the inserted cylinders with a waxy substance at the down part of piston (1) at position (7).

When the piston (1) is pushed down, the liquid in reservoir 3 flows up through the space between the cylinders and leaks through holes (9) into the waste storage inside the inner tube and simultaneously rinses the surface (5). When the piston is down, the measurement is carried out.

FIG. 3. FIG. 3 A (the cross-section is rectangular as in FIG. 1) describes the starting position as in FIG. 1 from side. In FIG. B, the piston is being pressed down so that the liquid from reservoir (3) flows through a thin channel in such a way that it effectively rinses the analytical surface (5). FIG. 3 exemplifies a construction of a liquid-proof tightening of the down tip of piston. This can be achieved by an distal extension of the piston and tightening material like rubber or plastic with a fit snug. The down part of the piston fits exactly against the outer wall deviating in this respect from constructions in FIGS. 1 and 2. In FIG. 3 B, the pathway of the liquid from storage reservoir (3) to waste reservoir (8) is illustrated with arrows. For the liquid flow, the piston has hole (9). The very initial movement of the piston is allowed by either a small amount of air in the storage reservoir (3) or a flexible bellows in the liquid. For clarity, FIG. 1 does not show the liquid absorbing material as in FIG. 1.

DETAILED DESCRIPTION OF THE INVENTION

The invention describes a measuring cell (chamber, cassette, or cartridge) which can be used for performing an analysis is a sealed chamber. The cell consists of two parts, outer (cover, cylinder part, cartridge casing) and inner parts (piston or test chip, or test strip). The piston can be pushed inside the cylinder in such way that cylinder and piston form an integral unity which does not leak liquid outside. When the piston is at the down position the system can be subjected to a measuring process. Such a measuring cell can be also stored for a later measurement or to be sent elsewhere to be measured. FIGS. 1-3 illustrate three different ways of realizing the same principle. The Figures describe only the principles of realization and do not consider the exact or relative measures of the acting parts. An essential feature of the present invention is a piston and a cylinder, relative movements of which are exploited for achieving the desired measurement process.

The piston part or inner part is related to normal test strips commonly used for performing rapid tests. For example, sugar analyses of urine or pregnancy tests often use a plastic strip furnished with structures which contain the needed reagents and label compounds allowing to estimate the amount of the analyte in sample by a color change.

Analyses requiring high accuracy and reproducibility are often made on the surface of a plastic plate with the principle of bioaffinity. The plastic is coated with antibodies or other biomolecules, like DNA probes, which can selectively bind the analytes. In the present invention, such a surface is called as analytically active surface or active surface. It is often created on a surface of a vessel, like a microtiter plate wells. The sample and needed reagents are brought into the vessel and the reaction is allowed to complete followed by washing the unused reagents away.

The next reactions and measurement can be carried out in the same vessel with proper solutions. An example for such a test concept is the DELFIA technology of PerkinElmer-Wallac (PerkinElmer Finland Co., Turku, Finland) employing luminescent label molecules excited with light pulses. The luminescent labels can also be excited with electrical pulses as illustrated with the CECL-technique (Cathodic Electro Chemi Luminescence, www.Labmaster.fi). Commonly used ELISA method is based the use of enzymes for the multiplication of the measurable signal. Often produced color is measured photometrically. In all these techniques vessels and test strips are prone to contaminations in the measuring conditions. The measuring includes many steps and more than one technical device in addition to the measuring instrument (e.g. photometer, fluorometer, luminometer).

Devices containing various complex capillary and micro technical details have been developed for carrying out the above-described analyses. Their drawback is the very demanding production technology and the false results originating from the tiny dimensions.

It was found in the present invention that the objective of applying micro and nano technical details is not sensible in majority of cases and simple closed contamination-free measuring cells can be elaborated to solve complicated analytical problems. In the present invention, the traditional role of the measuring vessel and the analytically active surface has been interchanged. The passive parts, which are used in the common test chip to make the manipulation easier, are employed in the present invention to carry out processes needed for the analysis: the test chips are used for moving liquids in addition to chips' normal use.

The cover part (chassis) of the test chip (2 in FIGS. 1-3), or outer part of the cell, is equally well employed as an active part. Instead of special expensive and complex washing systems, the present invention exploits the mechanical movement between the test chip (1, in FIGS. 1-3) and its cover (2, in FIGS. 1-3) to provide the washing. A resulting thin liquid, preferably of turbulent rather than laminar, flow obtained by the movement of (1) and (2) makes it possible to achieve very effective washing of a surface and/or to use only tiny liquid volumes. When using small liquid volumes for washing, considerably savings in reagent costs will be achieved.

According to the present invention the "piston" (1) is composed of a flat or cylindrical component (test chip, strip) containing the analytically active area (5). This area may have been prepared by introducing, for example, antibody or DNA probe onto a plastic strip by adsorption or by covalent coating. The details of preparation of the active area depend on the physico-chemical method by which the measurement itself is realized. For example, a plastic plate or related material is covered with a drop of antibody solution and antibody is allowed to attach to the surface. Unbound antibody is then washed off after a certain time. Depending on the assay principle also other reagents can be brought onto the surface. So-called sandwich assay exploits, in addition, another type of monoclonal (secondary) antibody which is labeled with a luminescent compound or an enzyme. These labeled secondary antibodies can be brought onto the surface also after the sample or as mixed with the sample. If the label substances are excited with light, no other special part in the measuring cell is required. If the label is excited by electricity (anodic or cathodic pulses), the test strip must contain also anode and cathode and their wiring to the excitation electronics.

The analytically active surface (5, in FIGS. 1-3) can be covered by a filter material which removes particles from the sample and/or introduces the sample smoothly onto the surface. If removal of the filter is required, the present invention teaches to direct the liquid flow in such a way that it will push the filter away from the surface and allow the active surface to be free during the excitation and light measurement.

The sample to be analyzed is placed onto the analytically active surface (containing a filter or not). The test strip is placed inside the cell so that the sample can be introduced through a small hole in the cell (6 in FIG. 1). The hole is preferably opened only for the period of application; otherwise it is closed with an adhesive tape or stopper. After the application of the sample, a predetermined time will be waited to allow reaction to take place. After that, the piston is pushed downwards so that piston will replace liquid in the reservoir and concomitantly push the liquid primarily over the analytically active surface thereby washing the surface. The washing liquid is constantly fresh as opposite to the usual batch washing. Since the moving liquid layer is relatively small (0.1-2.5 mm), the axial diffusion velocity of the sample component is negligible compared to horizontal diffusion of the reacting components.

The efficiency of the washing can be adjusted by adjusting the thickness of the liquid layer and/or changing the axial velocity of the piston. The increase of the velocity of the piston changes the liquid flow from laminar to turbulent. Typical specific feature of the invention is the extremely efficient controllable washing of the active surface that is significantly better than with the mode of batch washing. The batch washing means that a certain amount of liquid is injected and sucked away several times. With batch washing the consumption of washing liquid is significantly higher as regards to washing result than with the method of the present invention.

The piston can be pushed manually but it is also feasible to construct an electrical motor-driven instrument and to include timing automatics in it. All this can be included in the measuring instrument.

When the piston reaches its lowest position, the measurement can be in many cases done immediately. In the case of luminescence or absorbance, the measuring cell must contain proper windows transmitting the required wavelengths of light. It may be advantageous to make the whole outer part (i.e. cover or chassis, 2) of the cell of transparent material like polystyrene. The window material of the chassis can also be dyed which can serve as filter for the light. The efficiency of the light detection can be improved with reflectors and mirrors inside the measuring cell and/or instrument's measuring chamber. In a cylindrical construction, illustrated in FIG. 2, analytically active part can be the whole ring (band) around the cylinder. This is not any hindrance since the generated light can be readily guided to a light sensor (e.g. photomultiplier) with reflectors. For radioactive labels, annular detectors can be used.

When the invention is applied to ELISA or related tests, wherein the label is an enzyme, the liquid reservoir can involve two or more of compartments. The first chamber can contain a washing liquid while the next contains the substrate solution of the enzyme. The compartments can be separated with a breach-able membrane, for example.

FIGS. 1-3 indicate the mode of realization of the invention when the analytically active surface is of plane form. The surface can also include grooves, papillae, bars etc., which increase the effective surface area. Especially with ELISA tests using absorbance measurement, it may be advantageous to use a cylindrical (or any other form) hole (or holes) as the source the active surface. For example in FIG. 1 A, it could have been bored horizontally, partly or totally, through the test strip (piston). In such a construction the piston can fit rather exactly into the liquid reservoir. The washing liquid and substrate solution flow is arranged through the horizontal chamber with the aid of vertically bored hole(s) in the piston to the waste reservoir. At the end of the process, the horizontal chamber is full of substrate solution of the enzyme. The enzyme activity (proportional to the amount of the analyte) is measured through the chamber with the generated color intensity after a suitable time interval.

An essential feature of the present invention is that the construction of the cell is simple and integral. Its manipulations are safe to the user even with dangerous samples, like body fluids of diseased people. Furthermore, the measuring cell tolerates different storage conditions. The devices are preferably packed into sealed individual packages. The hole for the sample application is closed and is opened only for the application of the sample. To prevent any kind of leakages from the cell, it is preferably further supplied with a liquid absorbing material, like soft plastic, polyethylene glycol, or cotton. When the upper end of the liquid reservoir closes the space of the analytically active area (not drawn in FIGS. 1-3 for clarity) while the cap of the piston closes the whole cell. The measuring cell can be stored for longer periods of time without significant changes in the properties even when it contains the analytical samples.

FIG. 1 illustrates a construction wherein the liquid storage is closed with a thin membrane (drawn also in FIG. 4) which is broken by the down-movement of the piston. FIG. 2 illustrates a construction wherein the respective point is circularly tightened with a waxy substance which decomposes by the movement of the piston. In FIG. 3, the tip of the piston is snugly fitted into the chamber which closes the channels for liquids.

A large variety of materials can be chosen to make the measuring cells. The choice depends on the specific applications and on the detection technology. In general polystyrene and other transparent plastics are preferable. The technologies which suit to manufacturing of the measuring cells from plastic are injection molding and casting.

As implied above, the measuring cell of the present invention is adaptable to many kinds of analyses and measuring techniques. The invention is further described below with non-limiting examples. The examples illustrate a detection technology using electrical excitation of luminescent label molecules on a routine test strip of the technology (www.Labmaster.fi) and ELISA method using a polystyrene strip as the piston. Both examples exploited a separately fabricated cover part (chamber).

EXAMPLE 1

A piece of doped 1-mm silicon (4×9 mm) was mounted into a polystyrene plate of about 3 mm thickness (length 5 cm, width 1.2 cm). The silicon piece was oxidized to make resistor film of 4 nm thickness on it (www.Labmaster.fi). The test strip was biochemically prepared in such a way that it can analyze C-reactive protein (CRP) from human blood. The silicon piece was covered with a filter membrane including dried secondary antibody labeled with a terbium chelate. The test strip was equipped with electrical contact to cathode with an adhesive copper film while anode was a stainless steel spike pushed through the bottom of the liquid reservoir (device as in FIG. 1).

The liquid reservoir contained 1 ml of standard electrolyte solution which served as washing as measuring buffer. The first prototypes were prepared by using commercially available cuvettes for spectrophotometry which were essentially like the cover part of the cells described in FIG. 1. Hole was bored in the wall of the cover part (as 6 in FIG. 1). The tip of the test strip was machined diagonal (45 degree) as in FIG. 1 to optimize the liquid flow to focus onto the silicon surface. The gap between the cylinder and piston at the place of analytically active area was 1.5 mm and at the opposite site of the piston 0.1 mm. The piston was pressed manually simultaneously observing the liquid flow. When the flow reached the membrane above the silicon piece, membrane was detached and was directed upwards with the liquid flow. The piston was pressed down and the mode (Labmaster Ltd., Turku, Finland). When measuring unknown patient samples and CRP standard solutions, similar results were obtained within experimental errors as those obtained when the test strip were extensively washed batchwisely.

EXAMPLE 2

The experiment of Example 1 was made with a test strip wherein anode and cathode were integrated onto same level on the plastic strip. From both of the poles electrical contacts were made onto the top of the (piston) strip. The function and results of the experiment were similar to those of Example 1.

EXAMPLE 3

The function of device with construction of FIG. 2 was tested with the ELISA method. The analytically active circular surface was coated with CRP-catching antibodies, washed and saturated with albumin solution with standard methods in literature. A sample and a secondary antibody labeled with alkaline phosphatase were mixed and were pipetted onto the active area through hole 6 (FIG. 2) so that the liquid started to spill over through holes 9. After 20 min the piston was pushed down during 5 seconds into liquid 3 which was 1 ml of substrate solution of alkaline phosphatase. A part of the substrate served as the washing liquid. After 15 min, the generated yellow color was measured with absorption photometry directly through the plastic tubes. Since the optical thickness in this construction was only about 2 mm, and the width of the light beam was narrow, this method was poor in sensitivity. These drawbacks can be avoided with proper arrangements which a person skilled in the art can make. Therefore, the constructions of the present invention are useful also for ELISA measurements.

EXAMPLE 4

FIG. 3 illustrates a construction which employs tight fitting between cylinder (cover part) and piston (test strip) at the tip of the strip. The construction in FIG. 3 is not symmetrical but the piston situates in the front part of the cover. A thin rectangular channel exists in front of the strip piston which is in contact to the liquid reservoir from down. When the piston is down (in measuring stage), a thin layer of liquid in front of measuring window does not interfere the results, especially if the liquid is colorless. The construction of FIG. 3 showed good washing properties.

The invention claimed is:

1. A measuring cell for carrying out chemical and biochemical analyses, the cell comprising:
    a cylindrical vessel having a bottom and an outer wall having a transparent measuring window; and
    a solid inner part being a piston and being capable of moving up and down inside the vessel; wherein
        the piston comprises a first end being a cap for the cell and a second end being a tip of the piston and an active surface area in between the first and second end, and the piston comprises an initial uplifted position and a measuring position when pressed down inside the vessel;
    the outer wall of the vessel having substantially the same height as the piston and the vessel having a liquid compartment and a waste storage at the bottom of the vessel and the liquid compartment and waste storage being separated from each other by a vertical wall shorter than the outer wall of the vessel and wherein the liquid compartment is filled with a washing reagent;

the vessel having at least one hole on a side of the outer wall above the liquid compartment for insertion of a sample on the active surface area of the piston when the piston is in the initial uplifted position;

the active surface area comprising in dry stage components and reagents necessary to carry out the analysis, wherein the active surface area is located on the piston such that when the piston is in the measuring position the active surface area is in the liquid compartment;

the washing reagent washing the active surface area containing the dry stage components, reagents and the sample when the piston is pressed down to the measuring position, and the washing liquid flowing to the waste storage over the wall separating the liquid compartment and the waste storage; and wherein the cell transforms from an initial preparedness stage to a measuring stage when the piston is pressed down and the active surface is washed with washing liquid and a reaction on the active surface area creates a measurable signal that can be measured through the window of the outer wall and the signal is correlated to an amount of an analyte in the sample.

2. The measuring cell according to claim 1 wherein the sample is of biological origin.

3. The measuring cells according to claim 1 wherein the active surface area is coated with specific materials to carry out an immune-or a nucleic acid bioaffinity reaction.

4. The measuring cell according to claim 1 wherein the active surface area contains label molecules and the measurement is carried out with electrical excitation of the label molecules and analysis results are expressed as luminescence intensity.

5. The measuring cell according to claim 1 wherein the measureable signal created on the active surface area is measured by using electromagnetic radiation.

6. The measuring cell according to claim 1 wherein the maasureable signal created on the active surface is created by an enzyme reaction.

7. The measuring cell according to claim 1 wherein the measureable signal is produced by radioactive label components.

8. The analytical measuring cell according to claim 1, wherein the liquid compartment is covered with a membrane and the tip of the piston breaks the membrane when the piston is pressed down into the measuring position allowing the washing liquid to wash the active surface area and flow into the waste storage.

9. The analytical measuring cell according to claim 1 wherein the liquid compartment is divided into multiple compartments separated by a membrane and each compartment comprises different solutions to interact with the active surface area to carry out one of washing, chemical or enzymatic reaction, and measurement steps while the the active surface area of the piston moves through the compartments and replaces liquid in the compartments of the reservoir.

10. The measuring cell according to claim 1 wherein the active surface area is covered with a filter, removable by eruption of liquid from the liquid compartment generated by the movement of the piston into the measuring position.

11. The measuring cell of claim 1, wherein the hole in the side of the outer wall is open only when the sample is inserted onto the active surface area.

12. A method to measure an analyte in a closed system, wherein the method comprises the steps of:
a) providing a measuring cell comprising a cylindrical vessel having a bottom, an outer wall having a transparent measuring window and a liquid compartment at the bottom of the vessel; and
a solid inner part being a piston; wherein
the piston comprises a first end being a cap of the cell and a second end being a tip, and an active surface area coated with a dry stage reagent and located in between the first and second end; wherein the piston comprises an initial uplifted position and a measuring position when pressed inside the vessel; and a side of the outer wall having at least one hole located at the same level as the active surface area of the piston when the piston is in the initial uplifted position;
b) introducing the sample onto the active surface area of the piston through the at least one hole located on the side of the outer wall and allowing a reaction to take place on the active surface area when the sample contacts the reagent;
c) pressing the piston into the vessel, and inducing the tip of the piston to protrude the liquid compartment causing the liquid to flow over the active surface area and washing off analytes not attached to the active surface area; and
d) measuring the analytes bound on the active surface by measuring a signal emitted from the reaction on the active area through a window of the outer wall.

13. The method of claim 12, wherein the sample is a biological sample.

14. The method of claim 12, wherein the liquid compartment is divided into multiple reservoirs of liquids and wherein in step c) pushing the inner part of the piston into the vessel induces the tip of the piston to protrude the multiple reservoirs one at a time and the liquids in the multiple reservoirs washes the active surface area one at a time.

15. The measuring cell of claim 1, wherein the outer wall of the vessel is transparent.

16. The measuring cell of claim 11, wherein the hole on the side of the outer wall is covered with a removable stopper.

17. The measuring cell of claim 1, wherein the piston comprises liquid absorbing material underneath the cap.

18. The measuring cell of claim 1, wherein the piston is cylindrical and the active surface area is around the cylindrical piston.

19. the measuring cell of claim 1, wherein the piston is flat.

20. A closed single use measuring cell for measuring an analyte in a sample, the cell comprising a cylindrical vessel and a flat or cylindrical piston and the cell having preparedness stage and a measuring stage, wherein the vessel comprises a bottom and at least a partially transparent outer wall, and a side of the outer wall having at least one hole,
the vessel further having a liquid compartment and a waste compartment at the bottom of the vessel separated from each other by a vertical wall shorter than the outer wall of the vessel,
the piston having a first end and a second end and in between the first and second end, and an active surface area comprising dry stage reagents capable of reacting with the analyte in a sample,
and wherein in the preparedness stage the piston is in an uplifted position and the active surface is located at the level of the hole of the side of the outer wall, whereby the sample can be introduced onto the active surface area through the hole; and the liquid compartment contains a washing liquid, and wherein in the measurement stage the piston is pressed down and the washing liquid moves from the liquid compartment into the waste compartment as the piston fills the liquid compartment wherein the active surface area is located such that a measurable signal caused by a reaction between the reagent and the analyte in the sample can be measured through the at least partly transparent outer wall.

* * * * *